US00PP11681P

United States Patent [19]

Lemon

[11] Patent Number: Plant 11,681

[45] Date of Patent: Dec. 12, 2000

[54] VARIETY OF GERANIUM NAMED 'JESSICA'

[75] Inventor: David G. Lemon, Lompoc, Calif.

[73] Assignee: Oglevee, Ltd., Connellsville, Pa.

[21] Appl. No.: 09/162,745

[22] Filed: Sep. 29, 1998

[51] Int. Cl.[7] ..... A01H 5/00

[52] U.S. Cl. ..... Plt./329

[58] Field of Search ..... Plt./329, 330, 325, Plt./324, 328, 331

[56] References Cited

U.S. PATENT DOCUMENTS

| | | | |
|---|---|---|---|
| P.P. 6,017 | 9/1987 | Kirmann | Plt./331 |
| P.P. 8,192 | 3/1993 | Holden | Plt./330 |
| P.P. 10,018 | 9/1997 | Lemon | Plt./329 |

OTHER PUBLICATIONS

Hay, R., McQuown, G. and Beckett, K.. The Dictionary of House Plants. The Royal Hoticultural Society. pp. 197–198, 1974.

*Primary Examiner*—Howard J. Locker
*Assistant Examiner*—Michelle Kizilkaya
*Attorney, Agent, or Firm*—Webb Ziesentheim Logsdon Orkin & Hanson, P.C.

[57] ABSTRACT

'Jessica' is a new variety of *Pelargonium×hortorum* geranium plant which brings a new violet color to the floribunda geranium series. The plant habit, zoning and flowering traits are equal to or better than those already in the series. Cutting production and rooting time are similar to the current variety 'Elizabeth'. Growth habit is a neat mound which can be used well in containers, ground plantings or in hanging baskets.

1 Drawing Sheet

BACKGROUND OF THE INVENTION

This invention is directed to a new and distinct variety of *Pelargonium×hortorum* identified by the varietal name of 'Jessica', Breeder No. 4DG771 and Oglevee, Ltd. No. 5031. The new variety was discovered by David G. Lemon in a selected breeding program in Connellsville, Pa. The new variety is a selection from the crossing of the commercial variety 'Gypsy Girl', U.S. Plant Pat. No. 10,018 and the unpatented variety 'Pinto Violet'. The new variety was first asexually reproduced on Jan. 27, 1995 in Connellsville, Pa. It has been found to retain its distinctive characteristics through successive generations.

The new variety, when grown in a glass greenhouse in Connellsville, Pa. using full light, 60° F. night temperature and 68° F. day temperature and grown in soilless media with constant fertilizer at 200–250 ppm nitrogen and potassium, has a response time of six weeks to flowering from a rooted cutting potted in a 10 cm pot.

DESCRIPTION OF THE DRAWING

The accompanying photographic drawing illustrates the new variety, with the color being as nearly true as is possible with color illustrations of this type.

DESCRIPTION OF THE NEW PLANT

The following detailed descriptions set forth the characteristics of the new variety. The data which define these characteristics were collected from asexual reproductions carried out at Oglevee, Ltd., 152 Oglevee Lane, Connellsville, Pa. 15425. The color readinsgs on a test plant grown in a 26 cm pot were taken in 200–220 foot candles of cool white fluorescent light. Color references are primarily to the R.H.S. Colour Chart of The Royal Horticultural Society of London.

THE PLANT

Classification:
- *Botanical.*—*Pelargonium×hortorum.*
- *Varietal.*—Floribunda type of zonal geranium named 'Jessica'.

Form: Free basal branching; uniform mound.
Height: 18.0–19.0 cm above media when grown in 26 cm hanging baskets.
Growth: Self branching, medium mound habit with some cascading growth.
Strength: Free and early flowering, no mechanical pinching required, free standing, multipurpose uses.
Foliage: Stalked leaf attachment.
Leaves:
- *Size.*—7.0–7.5 cm across.
- *Shape.*—Reniform; cordate base.
- *Margin.*—Crenately lobed.
- *Texture.*—Lightly pubescent; slightly reflective.
- *Color.*—Top: Green Group 137C. Bottom: Yellow-Green Group 147B. Zone: Greyed-Purple Group 183A.
- *Ribs and veins.*—Venation: Palmate. Color: Yellow-Green Group 146C.

Petioles:
- *Length.*—5.5–6.5 cm.
- *Color.*—Yellow-Green Group 146B.

Stem:
- *Color.*—Yellow-Green Group 146C.
- *Internode length.*—1.8–3.0 cm.

THE BUD

Overall shape: Elliptical cluster.
Shape of individual bud: Elliptical when bud not showing color and peduncle not fully developed.
Size: 2.5–3.0 cm across when just showing color.

INFLORESCENCE

Blooming habit: Continuous; upright, floriferous blooming; double flowers.
Borne: Florets on pedicel, pedicel on peduncle, 4.5–7.0 cm above foliage.
Closed florets:
- *Bud size.*—0.9–1.5 cm.

Open florets:
- *Size of fully open bloom.*—Umbels: 5.5–7.5 cm across. Florets: 1.5–2.0 cm across.

*Color.*—Top: Overall color Red-Purple Group 61A. Red-Purple Group 61A at edge fading to Red-Purple Group 61B. Bottom: Red-Purple Group 61B. Eye: Present on upper petals; Red Group 43A.

*Petals.*—11–13 in number; obovate; margin entire; separate, not united; flat to slightly cupped.

Texture and appearance: Smooth, reflective.

Tonality from a distance: Bright violet flowers above medium green foliage with a zone present on the leaves.

Petaloids:

*Quantity.*—2–4.

*Shape.*—Twisted, irregular.

*Color.*—Top: Red-Purple Group 61A. Bottom: Red-Purple Group 61B.

Pedicel:

*Length.*—3.0–3.2 cm.

*Color.*—Yellow-Green Group 146B with Greyed-Purple Group 184A.

Peduncle:

*Length.*—16.0–18.0 cm long.

*Color.*—Yellow-Green Group 146B.

Disease resistance: Not known.

Lasting quality: Heat tolerant; bloom is very quick to recover after wet conditions.

REPRODUCTIVE ORGANS

Stamens:

*Anthers.*—1.0–2.0 mm long.

*Filaments.*—5.0–7.0 mm long; white with pink tips.

*Pollen color.*—Orange.

Pistils:

*Number.*—1; 5 to 6 parted.

*Length.*—7.0 mm.

*Stigma.*—Pink in color.

*Style.*—2.0 mm long.

*Ovaries.*—Pale green; 4.0–5.0 mm long.

Fruit: Some fruit observed.

GENERAL CHARACTERISTICS

The new variety brings a new violet color to the floribunda geranium series. The plant habit, zoning and flowering traits are equal to or better than those already in the series. Cutting production and rooting time are similar to the current variety 'Elizabeth' (U.S. Plant Pat. No. 8,192). Growth habit is a neat mound which can be used well in containers, ground plantings or in hanging baskets.

I claim:

1. A new and distinct variety of geranium plant named 'Jessica' as described and illustrated herein.

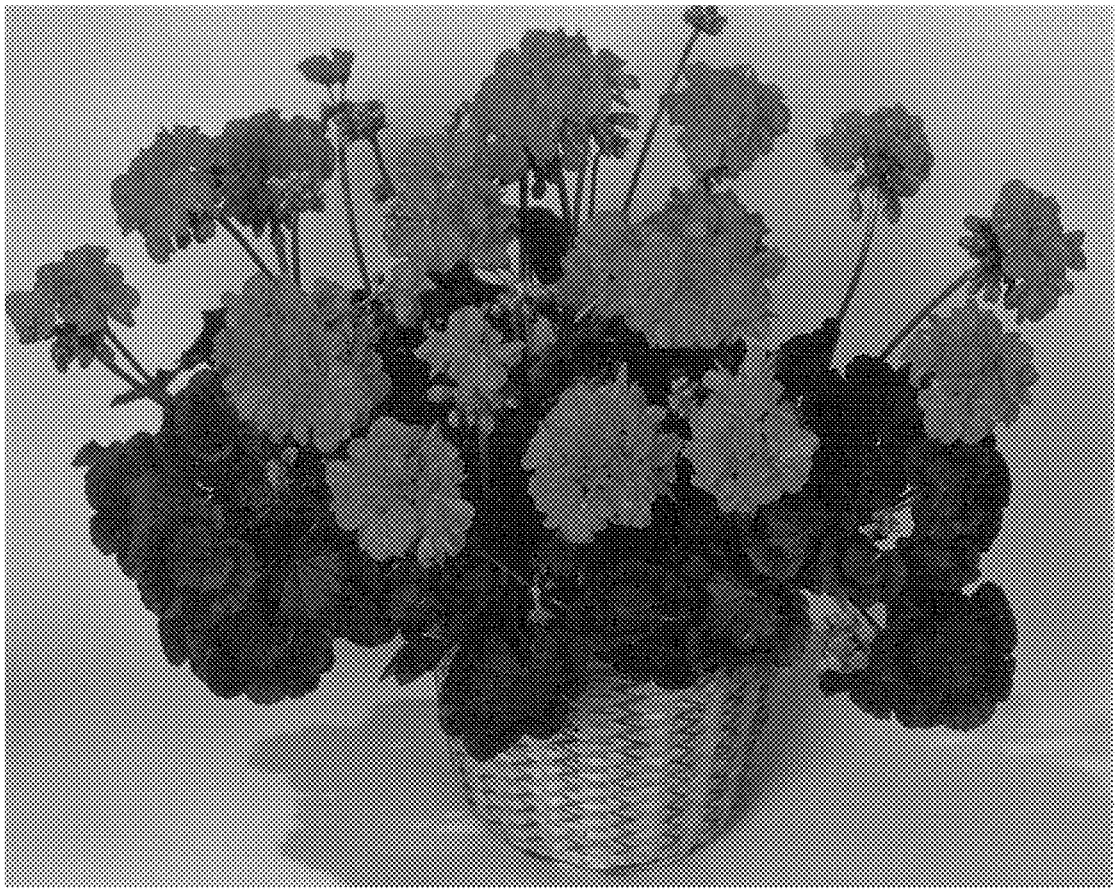

* * * * *